United States Patent
Ansley (10) Patent No.: US 9,671,383 B2
(45) Date of Patent: Jun. 6, 2017

(54) GAS-MONITORING APPARATUS FOR DETECTING BOWEL MOVEMENTS AND METHOD OF USE

(71) Applicant: Brad W. Ansley, Fairway, KS (US)

(72) Inventor: Brad W. Ansley, Fairway, KS (US)

(73) Assignee: Sensor Technologies, LLC, Fairway, KS (US)

( * ) Notice: Subject to any disclaimer, the term of this patent is extended or adjusted under 35 U.S.C. 154(b) by 185 days.

(21) Appl. No.: 14/606,494

(22) Filed: Jan. 27, 2015

(65) Prior Publication Data

US 2015/0212034 A1  Jul. 30, 2015

Related U.S. Application Data

(60) Provisional application No. 61/931,880, filed on Jan. 27, 2014.

(51) Int. Cl.
*G01N 27/416* (2006.01)
*G01N 33/00* (2006.01)
(Continued)

(52) U.S. Cl.
CPC ......... *G01N 33/0075* (2013.01); *A61F 13/42* (2013.01); *G01N 27/407* (2013.01);
(Continued)

(58) Field of Classification Search
CPC .. G01N 27/407; G01N 27/4141; G01N 33/48; G01N 33/497; G01N 2033/4977; A61B 5/6887–5/6898; A61B 5/42
See application file for complete search history.

(56) References Cited

U.S. PATENT DOCUMENTS

2006/0061477 A1  3/2006  Yeh
2008/0208016 A1*  8/2008  Hughes ............... A61B 5/0533
                                                    600/301
(Continued)

FOREIGN PATENT DOCUMENTS

JP  2000-245779 A  *  9/2000  ............... A61G 7/02
KR  20090119157      11/2009
(Continued)

OTHER PUBLICATIONS

JPO computer-generated English language translation of Mori et al. JP 2000-245779 A. Downloaded Sep. 26, 2016.*

(Continued)

*Primary Examiner* — Alexander Noguerola
(74) *Attorney, Agent, or Firm* — Law Office of Mark Brown, LLC; Christopher M. DeBacker (57) ABSTRACT

A room monitoring device designed and intended to detect a bowel movement (BM) of a person occupying the room, such as a baby or infant or an adult with special needs or in a care facility. The device tests the air for particular substances such as, but not limited to, methane and hydrogen sulfide. The test is performed multiple times per minute to reduce the chances of a false-positive detection. Once the device detects a positive BM, it alerts a user via Wi-Fi message, SMS text message, visual alerts (e.g., flashing lights), and/or audio alerts. This device may be paired with existing monitoring devices, such as a baby monitor with a remote camera.

19 Claims, 5 Drawing Sheets

(51) Int. Cl.
*G01N 33/497* (2006.01)
*G01N 27/407* (2006.01)
*G08B 21/12* (2006.01)
*A61B 5/00* (2006.01)
*A61F 13/42* (2006.01)

(52) U.S. Cl.
CPC ........... *G01N 33/497* (2013.01); *G08B 21/12* (2013.01); *A61B 5/6889* (2013.01); *A61B 5/6891* (2013.01); *A61F 2013/424* (2013.01)

(56) References Cited

U.S. PATENT DOCUMENTS

| | | |
|---|---|---|
| 2013/0110061 A1 | 5/2013 | Abraham et al. |
| 2014/0333442 A1 | 11/2014 | Carney |
| 2015/0212034 A1* | 7/2015 | Ansley ............... G01N 33/0075 204/403.01 |
| 2015/0330958 A1* | 11/2015 | Carney ................... A61F 13/42 73/23.34 |

FOREIGN PATENT DOCUMENTS

| | | | | |
|---|---|---|---|---|
| WO | WO 2012/126507 A | * | 9/2012 | ............. A61F 13/44 |
| WO | 2014098691 | | 6/2014 | |

OTHER PUBLICATIONS

"Extended European Search Report", EPO Application No. 16275013.7, May 27, 2016.

\* cited by examiner

GAS-MONITORING APPARATUS FOR DETECTING BOWEL MOVEMENTS AND METHOD OF USE

CROSS-REFERENCE TO RELATED APPLICATION

This application claims priority in U.S. Provisional Patent Application No. 61/931,880, filed Jan. 27, 2014, which is incorporated herein by reference.

BACKGROUND OF THE INVENTION

1. Field of the Invention

The present invention relates generally to a gas monitoring apparatus, and more specifically to an apparatus for monitoring humans, such as babies and infants, for bowel movements while they sleep using gas detecting elements.

2. Description of the Related Art

Often children wake crying during the night. This is often caused by a bowel movement (BM) happening during the night, and diaper rash or other discomforts can wake the child. It is impossible for a parent to know whether the child needs to have their diaper changed without physically checking the diaper for a BM. This can be detrimental when the child is crying for no reason, but the parent is forced to wake and check the child anyway.

Older adults in care or special needs patients would similarly benefit from a passive monitoring device to alert healthcare workers when the patient has suffered a BM. The worker would be alerted and could aid the patient to prevent bed sores etc.

What is needed is a method of actively monitoring a sleeping child and indicating if a bowel movement has occurred through the use of sensors which prevents unnecessary checking of diapers.

Heretofore there has not been available a system or method for detecting bowel movements with the advantages and features of the present invention.

SUMMARY OF THE INVENTION

The present invention generally provides a sensor apparatus for detecting gasses associated with bowel movements, such as, but not limited to, methane or hydrogen sulfide. In a preferred embodiment, the detector will take multiple samples over a desired time period to avoid false positives. The sensor apparatus is capable of alerting parents or others when a bowel movement is detected via sounds, lights, wireless message to a mobile device, or other means. This allows the sensor apparatus to be paired with other existing products (e.g., baby monitoring systems) without requiring additional equipment.

BRIEF DESCRIPTION OF THE DRAWINGS

The drawings constitute a part of this specification and include exemplary embodiments of the present invention illustrating various objects and features thereof.

FIG. 1 is a diagrammatic representation of a preferred embodiment of the present invention and elements with which it can communicate through.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate.

Additional examples include a mobile smart device including a display device for viewing a typical web browser or user interface will be commonly referred to throughout the following description. The type of device, computer, display, or user interface may vary when practicing an embodiment of the present invention. Said terminology will include the words specifically mentioned, derivatives thereof and words of similar meaning.

Gasses associated with bowel movements which would trigger the present invention include, but are not limited to: Indole ($C_8H_7N$), 3-methylindole ($C_9H_9N$), hydrogen Sulfide ($H_2S$), Amines, Ethanoic Acid ($C_2H_4O_2$), Butyric Acid ($C_4H_8O_2$), and methane ($CH_4$). These compounds are included amongst a number of outputs from human solid waste. For the purposes of the present application, any or all of these outputs should be considered to be used or to be detected for by the sensor system embodying the present invention.

Two types of gaseous sensor systems exist in the market place: (1) electrochemical sensors; and (2) metal oxide semiconductor (MOS) sensors. Either sensor type could be used in an embodiment of the present invention; however an MOS sensor is utilized in the preferred embodiment. The preferred sensor, MiCS-5524, is capable of measuring and detecting volatile organic compounds in a relative manner, such as by detecting changes in the environment, which provides an output of resistance change. The sensor can measure virtually any reducing and/or aromatic gas: such as ammonia, carbon monoxide, hydrogen sulfide etc., as well as any compound mentioned above. The MOS sensors are combusted by the presence of reducing gases at the sensor surface, and the release of electrons from these gases causes resistance across the sensor plate to drop.

Odors from human waste relate to foods eaten, not age. The emissions are essentially the same between infants and adults, but the present application focuses our technology on the most common denominator: hydrogen sulfide, but other gasses must also be tested for. As is well known, infants less than 6 months that are breast feeding do not emit much if any odor. Detecting latent odorless gasses would be highly beneficial to the purpose of the present invention.

II. Preferred Embodiment Bowel Movement (BM) Sensor System 2

Figure 1:
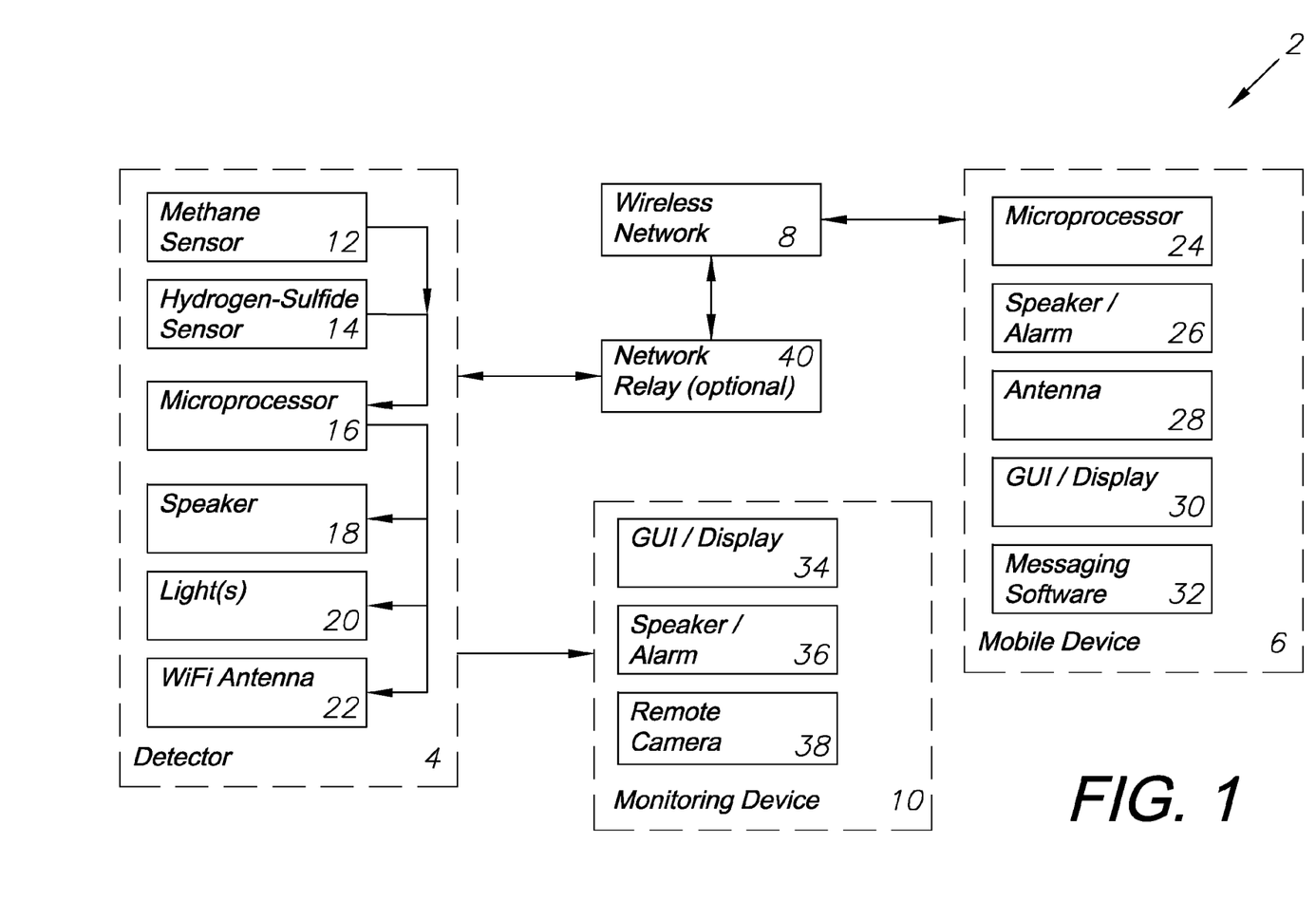

Referring to the figures in more detail, FIG. 1 shows a diagrammatic representation of a preferred BM sensor system 2, including a BM sensor/detector 4 for detecting a BM based upon gasses in the room, a mobile device 6 for receiving alerts from the BM sensor, and a wireless network 8 over which the mobile device 6 and the detector/sensor 4 communicate.

The detector 4 can also be used in conjunction with standard monitoring devices 10, such as a baby monitor with audio and/or video surveillance. Similarly, the detector 4 may access the wireless network 8 directly, or it may interact with a network relay 40 device for communicating between the network 8 and the detector 4. Alternatively, the relay 40 may only allow direct communication between the mobile device 6 and the detector 4, wherein other network access is limited or cut off.

As shown, the detector 4 includes sensors for detecting gas within the room, such as a methane sensor 12, a hydrogen sulfide sensor 14, or other sensors capable of detecting gasses which are emitted as part of solid or liquid human waste for detection with the BM detector 4. A microprocessor 16 receives data from the sensors 12, 14 and determines whether or not an alert should be sounded based upon preset or predetermined thresholds. The microprocessor can facilitate an alert by creating a noise amplified through a speaker 18, by flashing one or more lights 20 located on the detector 4, or by sending a wireless alert to the mobile device 6 using a Wi-Fi antenna 22 or other means of communication with the mobile device 6.

To increase the range of notifications, the audio or visual alerts created by the detector 4 through the use of the speaker 18 or the lights 20, respectively, a monitoring device 10 can be used. This monitoring device may or may not include a graphical user interface 34, a separate speaker or alarm 36 for the audio alert, and a remote camera 38 for the visual alert. This monitoring device 10 could be a standalone baby monitoring system to alert a parent if the baby is crying or not sleeping.

The mobile device 6, such as a standard smartphone device, includes a separate microprocessor 24, a speaker 26, an antenna 28, a graphical user interface (GUI) 30, and messaging software 32. The GUI may be a touchscreen interface, and may allow the user to directly make changes to the settings of the detector 4 using wireless access through software. The messaging software may include typical SMS messages sent using a service associated with the detector 4, or a completely separate software application or APP downloaded from a wireless network for use specifically with the detector 4.

Figure 2:
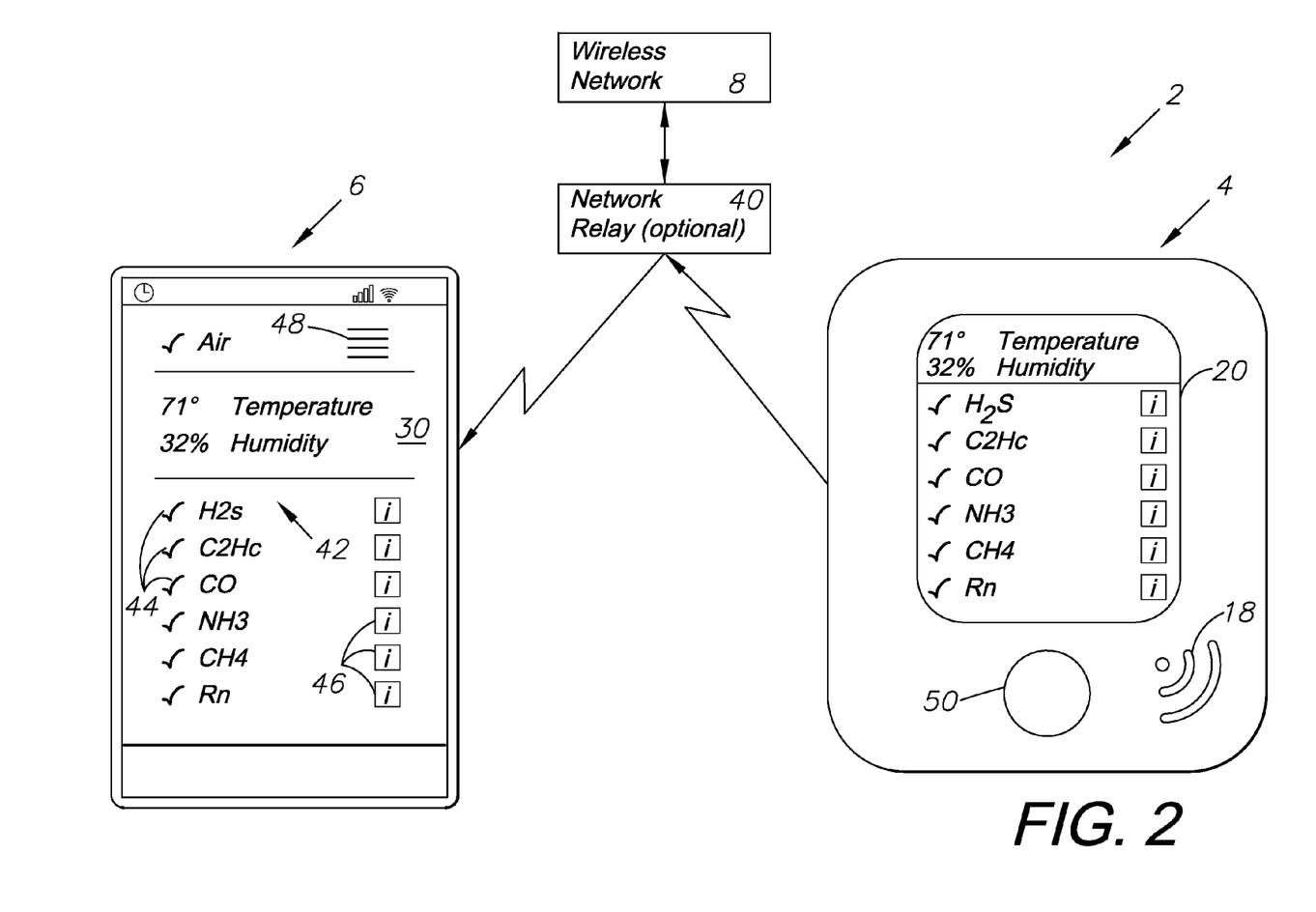
FIG. 2 is a diagram showing a simple relationship between various components of an embodiment of the present invention.

FIG. 2 shows a relationship between the mobile device 6 and the detector 4. The detector shown here includes controls 50 for accessing the settings of the detector directly. These settings can also be controlled wirelessly using the mobile device 6. A typical GUI 30 display screen on the mobile device includes such features as: ambient status 42 of the room being monitored; alert statuses 44 associated with various chemical compounds typically associated with a BM; information "buttons" 46 for accessing information about each substance or air quality value being detected for; and a settings pulldown button 48 for choosing different views or altering software settings of the mobile device 6 or of the detector 4.

The detector 4 may include controls 50 which allow direct access to the software or hardware settings of the detector. A speaker 18 located somewhere on the body of the detector delivers audio alerts, while a display or light 20 delivers visual alerts. Here, the GUI is also shown to include settings information that may be accessible via the mobile device 6. The GUI could simply flash when an alert is detected, may display the settings of the detector, or may otherwise give visual alerts to the user.

Figure 3:
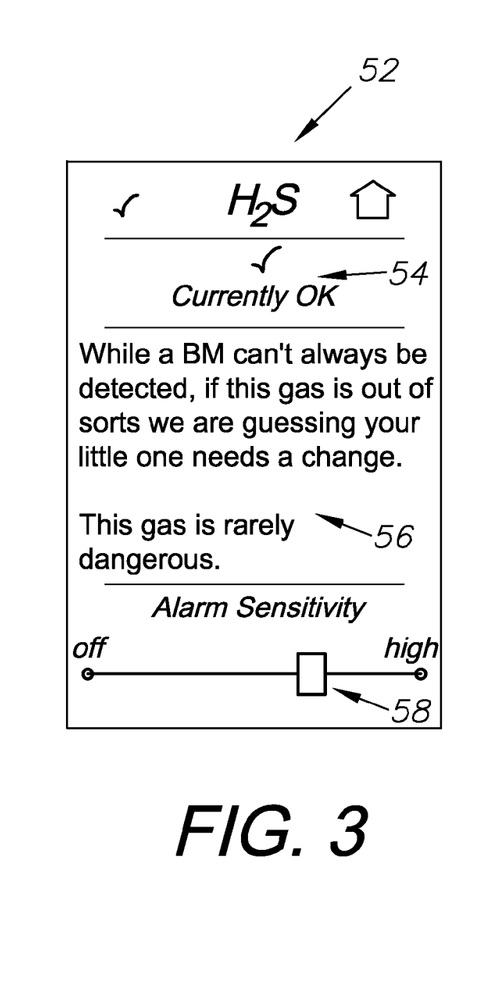
FIG. 3 is a diagrammatic representation of a sample status screen of a graphical user interface associated with the present invention.
Figure 4:
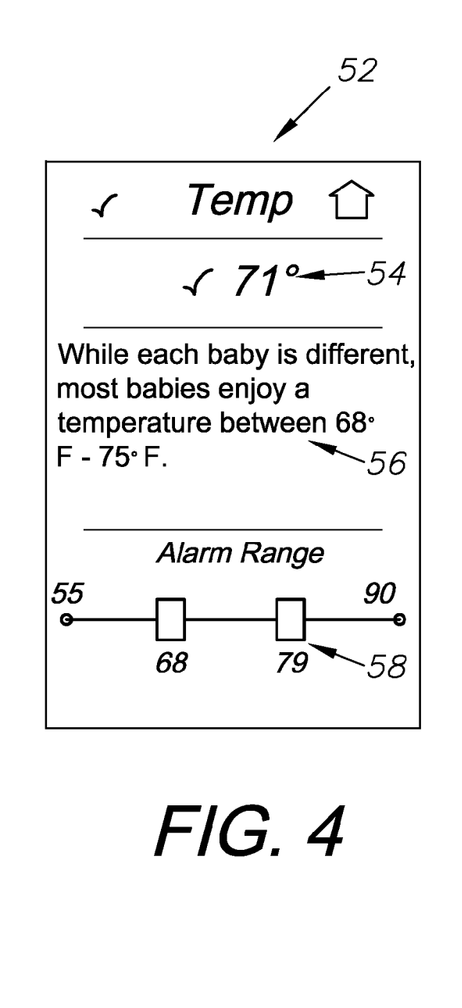
FIG. 4 is an alternative representation thereof.

FIGS. 3 and 4 are examples of GUI display screens 52 that may be accessible via the mobile device 6 or the display portion of the detector 4. FIG. 3, for example, shows the information status of H2S (Hydrogen Sulfide) being detected in the room by the detector 4. This display screen may be accessed by selecting the information button 46 associated with H2S on a home screen as shown in FIG. 2.

The status 54 of the selected element or room factor (e.g., temperature, gas presence, humidity) is displayed prominently, along with a checkmark or other indicator that everything is normal, or another indicator if the levels of the selected room factor or element are outside the set parameters. The parameters may be set using a scrolling bar 58 for determining when the alarm will be triggered by that room factor, if at all. A description of the element or room factor being reviewed is shown at 56. FIG. 4 shows a similar display, using air temperature as an example. Here, the sliding bar 58 includes an upper range and a lower range, allowing the user to customize that particular room factor even further.

Figure 5:
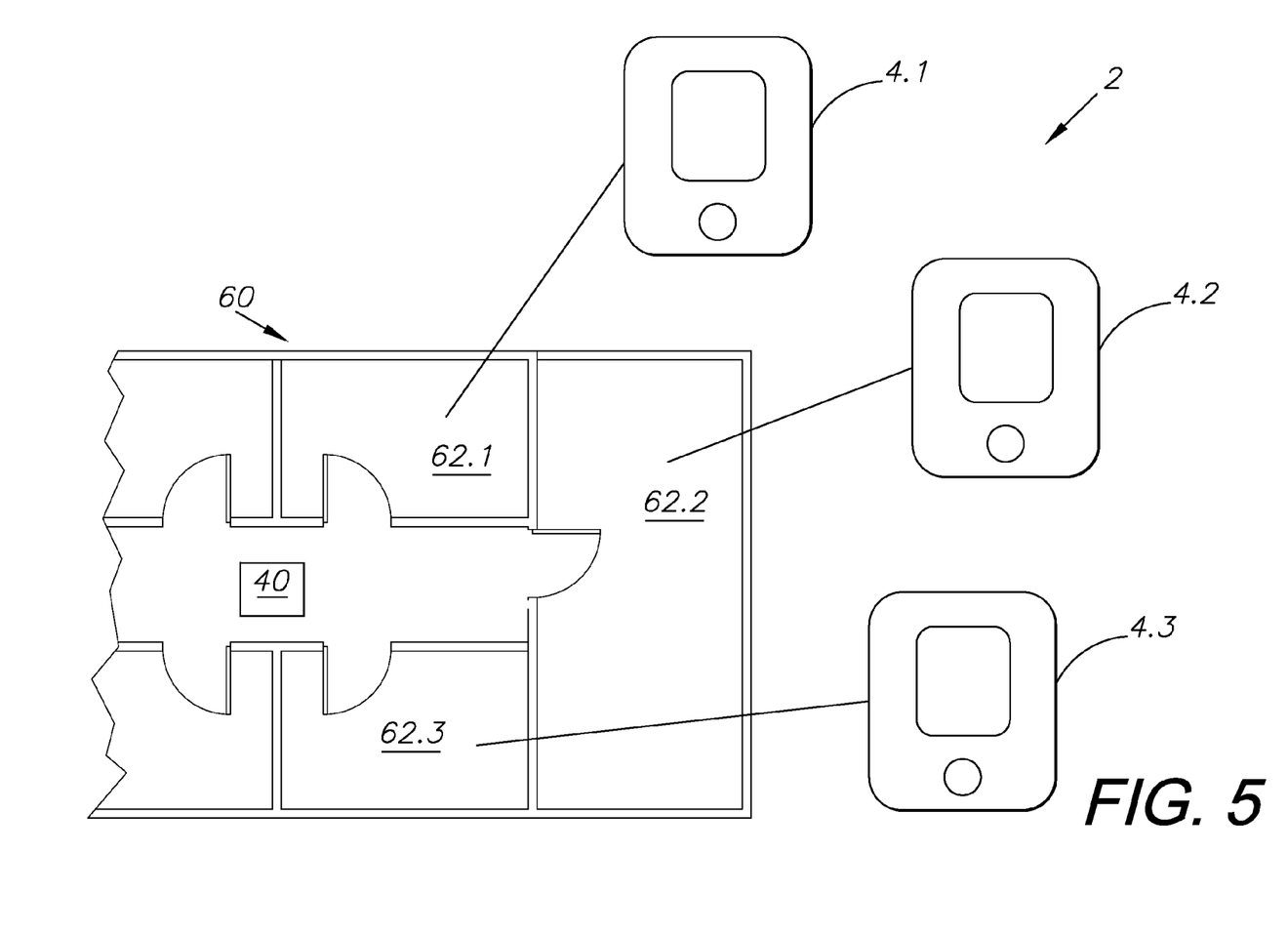
FIG. 5 is a diagrammatic representation of a floorplan having an embodiment of the present invention installed throughout.

FIG. 5 shows a floorplan 60 for a building, such as a home, hospital, or healthcare facility. Three rooms 62.1, 62.2, 62.3 are displayed, and three detectors 4.1, 4.2, and 4.3 are placed in the rooms respectively. A central relay 40 relays all data received from the detectors 4.1, 4.2, 4.3 to a stationary or mobile computing device, or multiple devices, to alert staff of a BM or other room irregularity. This setup is particularly useful in an adult care facility.

Figure 6:
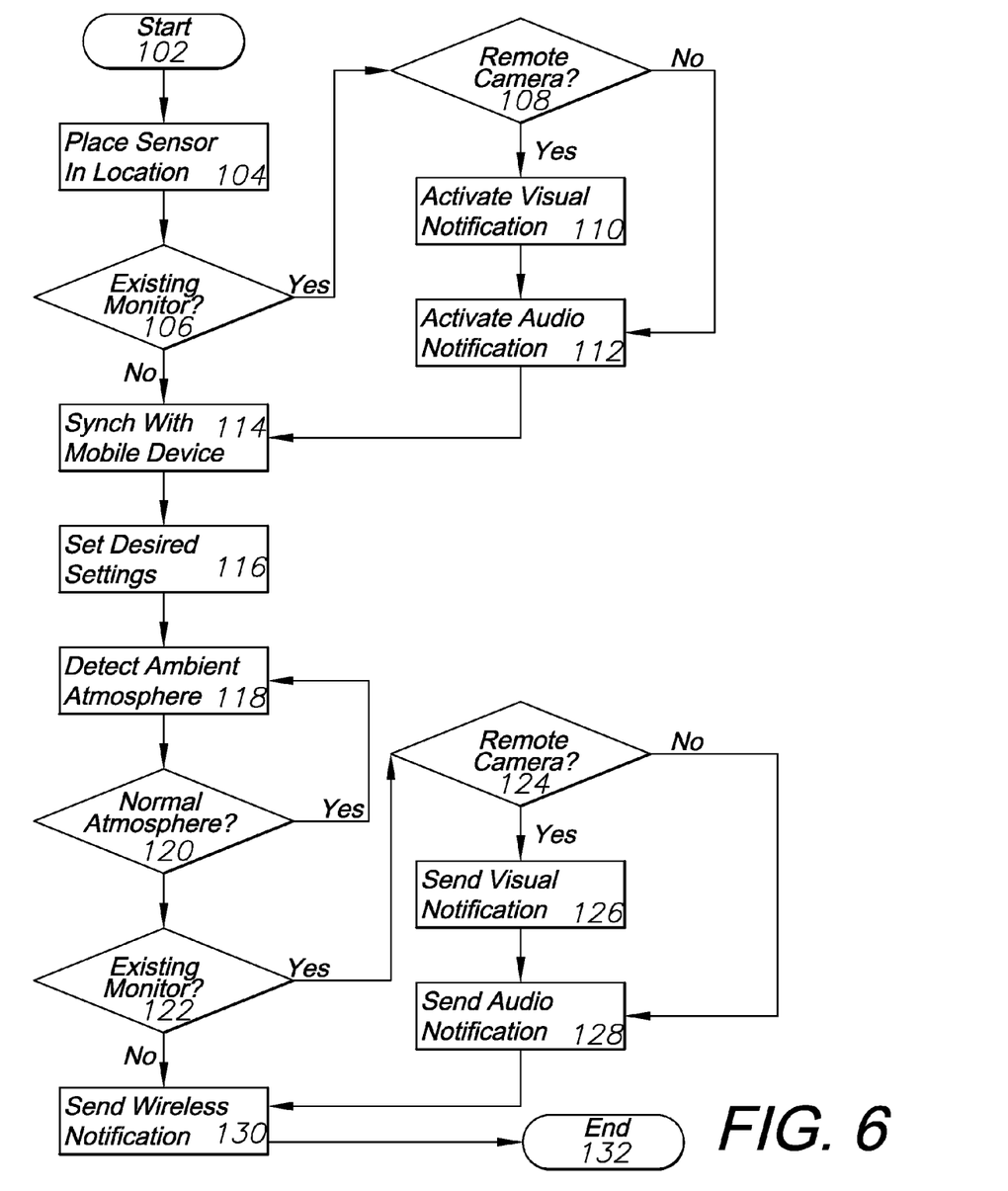
FIG. 6 is a flowchart diagramming the steps taken in practicing and embodiment of the present invention.

FIG. 6 is a flowchart demonstrating some steps taken while practicing a preferred embodiment of the present invention. The process starts at 102. A sensor is placed in a location at 104, preferably in a child or patient's room where a BM may occur while that person is sleeping. A check is performed at 106 whether an existing room monitoring device, such as a baby monitor, exists.

If an existing room monitoring device exists at 106, there is a determination at 108 if there is also a remote video camera associated with the existing room monitoring device. If yes, then the visual notification feature of the sensor is activate at 110. Either way, an audio notification is activated at 112.

Regardless of whether an existing monitor exists or not at 106, the sensor device is synched with one or more mobile computing devices at 114. This allows alert messages or other communication to be sent from the sensor/detector device and the mobile device(s). The user may also set desired settings 116 of the detector using the mobile computing device or the detector itself. These settings are the preferences for how sensitive the detector will be, and will be the basis for the ambient room atmosphere.

After this is all setup, the sensor actively monitors the ambient atmosphere of the room at 118. A check is constantly performed at 120 to determine whether the ambient room factors are within normal levels. If yes, then the cycle continues.

Once an abnormality is determined at 120, alert notifications must be sent out by the sensor device. If there is an existing monitoring device at 122 and a remote camera is present at 124, then the sensor will flash, light up, or otherwise activate a visual display that can be seen via a remote monitoring device connected to the remote camera at 126. At the same time, audio alerts, such as beeps or buzzing noise, will be produced by the sensor device at 128. This also will be sent through the monitoring device and played on a speaker associated with the existing monitoring device.

At the same time, or if there is no exiting monitor in place, a wireless notification is sent to the mobile device(s) associated with the sensor/detector at 130. These notifications may be sent via SMS messaging, or software specifically associated with the sensor/detector device, or through other means (e.g., automated telephone call). Once all alerts are sent, the process ends at 132. The process may automatically revert to a detection of ambient atmosphere at 118 once the issues associated with the alert have been addressed, or the system may require manual reset.

It is to be understood that while certain embodiments and/or aspects of the invention have been shown and described, the invention is not limited thereto and encompasses various other embodiments and aspects.

Having thus described the invention, what is claimed as new and desired to be secured by Letters Patent is:

1. A bowel movement (BM) detector system for placement in an occupied room, the system comprising:
   a BM detector comprising a housing, a microprocessor, and at least one gas sensor;
   said at least one gas sensor configured to test for the presence of a substance, and said sensor configured to provide testing data to said microprocessor;
   said BM detector further comprising a Wi-Fi antenna for communicating with a mobile computing device, said mobile computing device including a graphical user interface (GUI), a communications antenna, and a microprocessor;
   a room monitoring system including a microphone;
   a remote monitoring device comprising a speaker;
   said BM detector comprising a speaker configured to produce an audible alert upon the detection of said substance in the vicinity of said detector; and
   wherein said room monitoring system alerts the user via said remote monitoring device speaker.

2. The system of claim 1, wherein said substance is a substance chosen from the list comprising: Indole ($C_8H_7N$), 3-methylindole ($C_9H_9N$), hydrogen Sulfide ($H_2S$), Amines, Ethanoic Acid ($C_2H_4O_2$), Butyric Acid ($C_4H_8O_2$), and methane ($CH_4$).

3. The system of claim 1, wherein said at least one gas sensor is an electrochemical sensor.

4. The system of claim 1, wherein said at least one gas sensor is a metal oxide semiconductor (MOS) sensor.

5. The system of claim 1, further comprising:
   said at least one gas sensor configured to test for the presence of said substance at least twice over a predetermined time period; and
   wherein an alert is generated upon positive detection of said substance at each test over said predetermined time period.

6. The system of claim 1, further comprising a Wi-Fi transceiver configured to receive communication data from said BM detector and transmitting said communication data to said mobile computing device.

7. The system of claim 1, wherein said remote monitoring device comprises said mobile computing device.

8. The system of claim 7, further comprising:
   said mobile computing device including a software program including a user interface configured to relay information from said BM detector to the user;
   said software program comprising a messaging application configured to receive alert messages from said BM detector; and
   said software program further comprising an interface application for adjusting a plurality of range settings associated with said BM detector.

9. The system of claim 8, wherein said range of settings associated with said BM detector are selected from the list comprising: Indole ($C_8H_7N$) levels, 3-methylindole ($C_9H_9N$) levels, hydrogen Sulfide ($H_2S$) levels, Amine levels, Ethanoic Acid ($C_2H_4O_2$) levels, Butyric Acid ($C_4H_8O_2$) levels, methane ($CH_4$) levels, ambient temperature, and humidity.

10. The system of claim 9, further comprising an adjustable upper range limit for said range of settings, said adjustable upper range limit adjustable using said software program of said mobile computing device.

11. The system of claim 10, further comprising an adjustable lower range limit for said range of settings, said adjustable lower range limit adjustable using said software program of said mobile computing device.

12. The system of claim 1, further comprising:
   said room monitoring system comprising a remote camera, and said remote monitoring device comprising a video display for displaying a live video feed recorded by said remote camera;
   said BM detector comprising a lighted region of said BM detector housing configured to produce a visual alert upon the detection of said substance in the vicinity of said detector; and
   wherein said room monitoring system alerts the user via said remote monitoring device video display.

13. The system of claim 12, wherein said lighted region of said BM detector housing comprises a graphical user interface.

14. A bowel movement (BM) detector system for placement in an occupied room, the system comprising:
   a first BM detector comprising a housing, a microprocessor, and at least one metal oxide semiconductor (MOS) gas sensor configured to test for the presence of a substance in the air in the vicinity of said first BM detector, and said sensor configured to provide testing data to said microprocessor;
   said first BM detector being located in a first room;
   a mobile computing device, said mobile computing device including a graphical user interface (GUI), a communications antenna, and a microprocessor;
   wherein said substance is a substance chosen from the list comprising: Indole ($C_8H_7N$), 3-methylindole ($C_9H_9N$), hydrogen Sulfide ($H_2S$), Amines, Ethanoic Acid ($C_2H_4O_2$), Butyric Acid ($C_4H_8O_2$), and methane ($CH_4$);
   said first BM detector further comprising a Wi-Fi antenna for communicating with a Wi-Fi transceiver configured to receive communication data from said first BM detector and transmitting said communication data to said mobile computing device;

said first BM detector configured to test for the presence of said substance at least twice over a predetermined time period;
wherein an alert is generated upon positive detection of said substance at each test over said predetermined time period;
a room monitoring system comprising a microphone and a remote monitoring device comprising a speaker, said remote monitoring device configured to receive audio communications from said monitoring system microphone;
said BM detector comprising a speaker configured to produce an audible alert upon the detection of said substance in the vicinity of said detector; and
wherein said room monitoring system alerts the user via said remote monitoring device speaker.

15. The system of claim 14, further comprising:
a second BM detector comprising a housing, a microprocessor, and at least one gas sensor configured to test for the presence of a substance in the air in the vicinity of said first BM detector, and said sensor configured to provide testing data to said microprocessor;
said second BM detector being located in a second room; and
said second BM detector further comprising a Wi-Fi antenna for communicating with said Wi-Fi transceiver configured to receive communication data from said second BM detector and transmitting said communication data to said mobile computing device.

16. The system of claim 14, further comprising:
a room monitoring system comprising a microphone and a remote monitoring device comprising a speaker, said remote monitoring device configured to receive audio communications from said monitoring system microphone;
said first BM detector comprising a speaker configured to produce an audible alert upon the detection of said substance in the vicinity of said detector; and
wherein said room monitoring system alerts the user via said remote monitoring device speaker.

17. The system of claim 16, further comprising:
said room monitoring system comprising a remote camera, and said remote monitoring device comprising a video display for displaying a live video feed recorded by said remote camera;
said first BM detector comprising a lighted region of said first BM detector housing configured to produce a visual alert upon the detection of said substance in the vicinity of said detector; and
wherein said room monitoring system alerts the user via said remote monitoring device video display.

18. The system of claim 17, wherein said lighted region of said BM detector housing comprises a graphical user interface.

19. The system of claim 14, wherein said remote monitoring device comprises said mobile computing device.

* * * * *